United States Patent [19]

Taguchi et al.

[11] Patent Number: 4,870,193

[45] Date of Patent: Sep. 26, 1989

[54] PROCESS FOR PRODUCING SPIRO-ORTHOCARBONATE

[75] Inventors: Hiromu Taguchi; Kiyokazu Mizutani; Hiroyuki Kato, all of Aichi; Takeshi Endo, Kanagawa, all of Japan

[73] Assignee: Toagosei Chemical Industry Co., Ltd., Tokyo, Japan

[21] Appl. No.: 771,915

[22] Filed: Sep. 3, 1985

[30] Foreign Application Priority Data

Sep. 3, 1984 [JP] Japan ............................ 59-182721

[51] Int. Cl.[4] .......................................... C07D 317/12
[52] U.S. Cl. .................................... 549/334; 249/335
[58] Field of Search ............................... 549/334, 335

[56] References Cited

U.S. PATENT DOCUMENTS 3,379,693  4/1968  Hostettler et al. ............... 549/230

FOREIGN PATENT DOCUMENTS 3225818  2/1983  Fed. Rep. of Germany ...... 549/334

Primary Examiner—Glennon H. Hollrah
Assistant Examiner—A. A. Owens
Attorney, Agent, or Firm—Sughrue, Mion, Zinn, Macpeak & Seas

[57] ABSTRACT

A process for producing spiro-orthocarbonate having glycol unit (2) is described, which comprises reacting a spiro-orthocarbonate having glycol unit (1) which is different from glycol unit (2), with a glycol having glycol unit (2) to release a glycol having glycol unit (1).

19 Claims, 2 Drawing Sheets

PROCESS FOR PRODUCING SPIRO-ORTHOCARBONATE

FIELD OF THE INVENTION

The present invention relates to a process for easily and economically producing spiro-orthocarbonate, which is a polymerizable monomer showing volume expansion upon polymerization, and which is industrially useful as a matrix raw material for composite materials.

BACKGROUND OF THE INVENTION

Hitherto, spiro-orthocarbonate has been obtained by reacting glycol with di-n-butyl tin oxide and carbon disulfide as described, for example, in *Journal of Organic Chemistry*, Vol. 35, p. 2347 (1970) and *Polymer Preprints*, American Chemical Society, Division of Polymer Chemistry, Vol. 14, p. 1169 (1973). An example thereof is illustrated by formula (1)

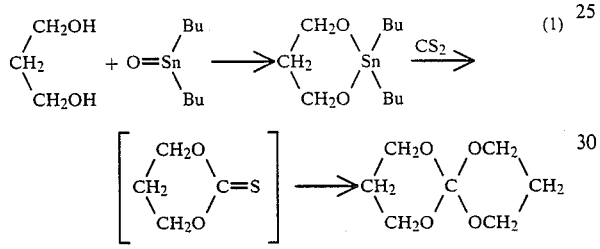

wherein Bu represents an n-butyl group.

However, this process has various problems, because an organic tin compound, which is very expensive, and carbon disulfide, which is difficult to handle because of its highly hazardous, are used as raw materials and the reaction step is complicated and separation of the desired product is very difficult.

Further, spiro-orthocarbonate can be produced by a reaction of glycol with tetraalkyl orthocarbonate as illustrated in formula (2)

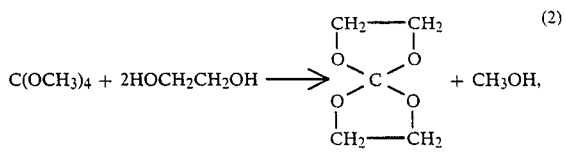

as described in Japanese Patent Application (OPI) No. 10582/83 (the term "OPI" as used herein means "published unexamined Japanese patent application"). This process is an excellent process for production, because substances which are easily handled are used as the raw materials, separation of the spiro-orthocarbonate is simply carried out, and the yield thereof is excellent. However, there is a problem in that the tetraalkyl orthocarbonate raw material is not readily available.

On the other hand, spiro-orthocarbonate can be also produced by reaction of an epoxide and cyclic carbonate as shown in formula (3)

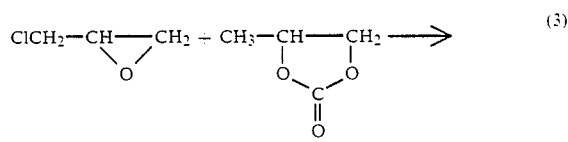

as described in Japanese Patent Application (OPI) No. 155385/84. In this process, spiro-orthocarbonate can be produced by one step in a high yield from raw materials which are easily handled. However, since the industrially available cyclic carbonates include only ethylenecarbonate and propylenecarbonate and the other raw material is an epoxide, this process is suitable only for the production of 1,4,6,9-tetraoxaspiro[4.4]nonane derivatives. Therefore, this process has the fault, for example, that 1,5,7,11-tetraoxspiro[5.5]undecane derivatives as shown in formula (4), etc. are difficult to produce, and only limited kinds of spiro-orthocarbonate can be produced.

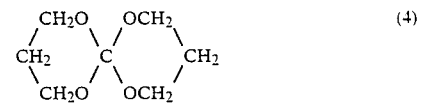

Further, it has been reported that 1,4,6,9-tetraoxaspiro[4.4]nonane derivatives are unsuitable as polymerizable monomers, because they cause decomposition in the case of carrying out, for example, ring-opening polymerization.

SUMMARY OF THE INVENTION

As is described above, there has not been any process by which various kinds of spiro-orthocarbonates can be produced from raw materials which can be industrially available or which can be economically and easily produced.

The present invention has solved the foregoing problems, and provides a process by which various kinds of spiro-orthocarbonate can be economically and easily produced, on an industrial scale.

That is, the present invention is a process for producing a spiro-orthocarbonate having glycol unit (2), which comprises reacting a spiro-orthocarbonate having glycol unit (1) which is different from glycol unit (2), with a glycol having glycol unit (2).

DETAILED DESCRIPTION OF THE INVENTION

Figure 1:
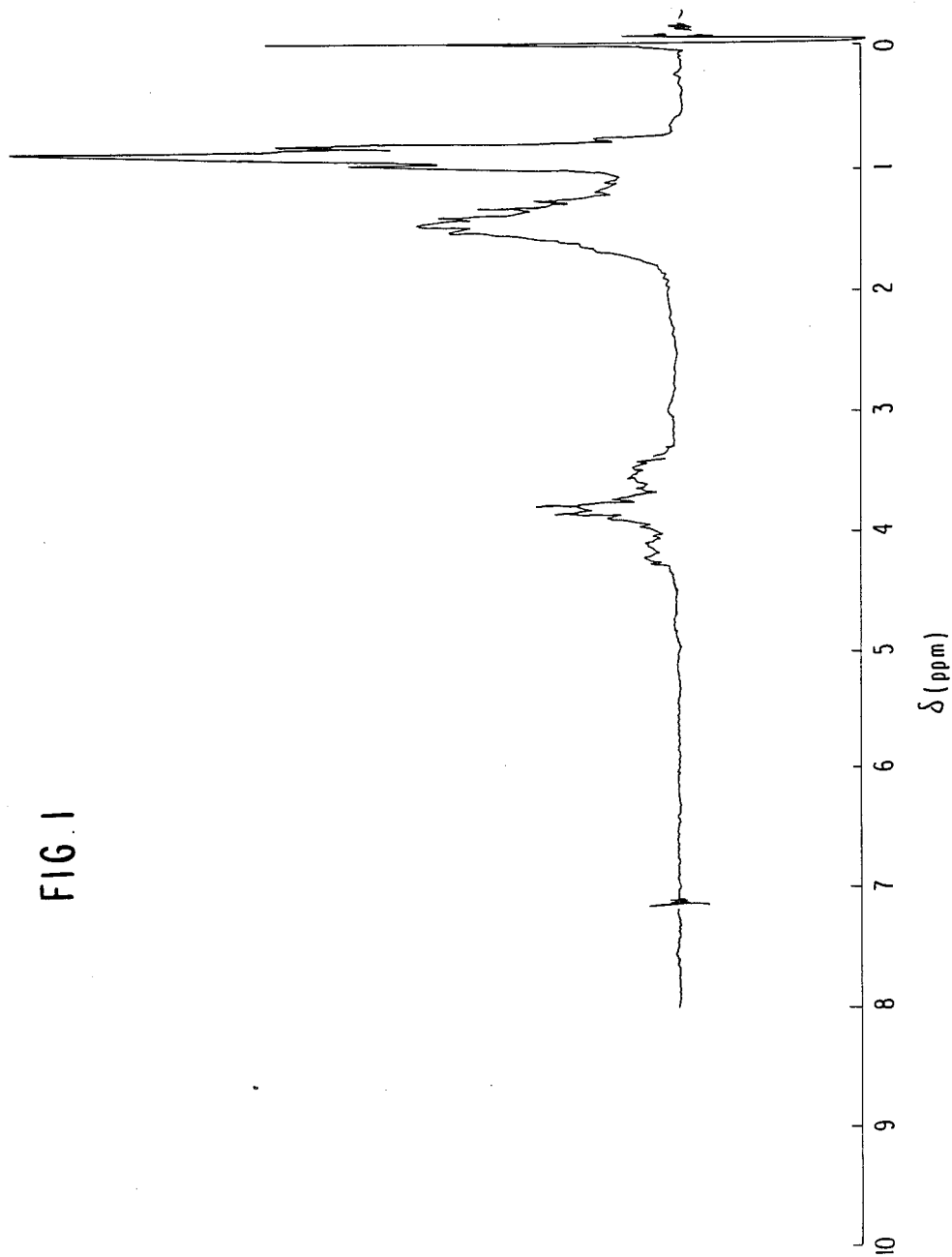
FIG. 1 is a NMR spectrum of 3,9-diethyl-2,8-dipropyl-1,5,7,11-tetraoxaspiro[5.5]undecane obtained in Example 5.

Raw material: spiro-orthocarbonate having glycol unit (1)

Spiro-orthocarbonates having glycol unit (1) used as a raw material in the present invention are stable substances which can be easily produced by a reaction between cyclic carbonate and epoxide as described above. They are not only economical to produce, but which can also be preserved for a long time.

As the cyclic carbonate, for example, ethylene carbonate, propylene carbonate, etc., are used, and as the epoxide, industrial products such as ethylene oxide, propylene oxide, epichlorohydrine, phenylglycidyl ether, etc., are used. Using them, 1,4,6,9-tetraoxaspiro[4.4]nonane, 2-methyl-1,4,6,9-tetraoxaspiro[4.4]nonane, 2,7-dimethyl-1,4,6,9-tetraoxaspiro[4.4]nonane, 2-chloromethyl-1,4,6,9-tetraoxaspiro[4.4]nonane, 2-chloromethyl-7-methyl-1,4,6,9-tetraoxaspiro[4.4]nonane, 2-phenoxymethyl-1,4,6,9-tetraoxaspiro[4.4]nonane, etc., can be produced.

Any of these spiro-orthocarbonates can be used as a raw material for the process of the present invention, but those which release a by-produced glycol having glycol unit (1) which has a lower boiling point than that of the other raw material glycol having glycol unit (2), by an ester interchange reaction are particularly preferred. Preferred examples include 1,4,6,9-tetraoxaspiro[4.4]nonane, or a derivative thereof, such as 2-methyl-1,4,6,9-tetraoxaspiro[4.4]nonane, 2,7-dimethyl-1,4,6,9-tetraoxxaspiro[4.4]nonane and 2-chloromethyl-1,4,6,9-tetraoxaspiro[4.4]nonane.

Raw material: glycol having glycol unit (2)

With respect to glycols having glycol unit (2), which are the other raw material, those having 0 to 2 carbon atoms intervening the two carbon atoms to which a hydroxy group is bonded are preferred because spiro-orthocarbonates suitable for production by an ester interchange reaction have a 5 to 7 membered ring, and 1,2-, and 1,3- and 1,4-diols are more preferred, with 1,3-diol being particularly preferred. In case of glycols having two hydroxy groups on the same carbon atom or those having 3 or more carbon atoms intervening the two carbon atoms to which a hydroxy group is bonded, cyclization is difficult to carry out because a spiro-orthocarbonate formed by the ester interchange has a 4-membered ring or a 8- or more membered ring.

Accordingly, specific examples of glycols suitable in the present invention to be used as the other raw material include 3-chloro-1,2-propanediol, 2-methylene-1,3-propanediol, 2,2-dimethylol-3,4-dihydro-2H-pyrane, 1,2-butanediol, 2,3-butanediol, 2-methyl-1,2-propanediol, 1,2-pentanediol, 2,3-pentanediol, 3-methyl-1,2-butanediol, 2-methyl-1,2-butanediol, 2,3-dimethyl-2,3-butanediol, 1,3-propanediol, 1,3-butanediol, 2,4-pentanediol, 2-methyl-2,4-butanediol, 2-methyl-2,4-pentanediol, 2,4-dimethyl-2,4-pentanediol, 2,3,3,4-tetramethyl-2,4-pentanediol, 2,2-dimethyl-1,3-propanediol, 2,2-dibromomethyl-1,3-propanediol, 2,2-dimethyl-1,3-butanediol, 3-butene-1,2-diol, 2-chloro-1,3-propanediol, phenylethylene glycol, 5-norbornene-2,2-dimethanol, 2-ethyl-1,3-hexanediol, 3-cyclohexene-1,1-dimethanol, norbornane-1,1-dimethanol, cyclohexane-1,1-dimethanol, etc.

Enter interchange reaction

In the following, the ester interchange reaction of the present invention is illustrated in detail. The ester interchange reaction is carried out by reacting the raw material spiro-orthocarbonate having glycol unit (1) with the raw material glycol having glycol unit (2), with heating, preferably in the presence of an ester interchange catalyst and a solvent. In this case, the by-produced glycol having glycol unit (1) is preferably removed out of the reaction system. For example, it is preferred to distill off the by-produced glycol from the system with a suitable solvent which forms an azeotropic mixture with the by-produced glycol.

Various desired spiro-orthocarbonates can be produced by this ester interchange reaction, by considering the molar ratio of the raw material spiro-orthocarbonate to the raw material glycol, the difference of the boiling points between the released by-produced glycol and the raw material glycol, the use of two or more kinds of the raw material glycol, and the like.

The raw material spiro-orthocarbonate and the raw material glycol are preferably used in a dry state, as far as possible. The raw material glycol is preferably used in an amount of 6 mols or less, and more preferably from 0.7 to 2.4 mols, per mol of the raw material spiro-orthocarbonate. When the solvent is used, the reaction can be allowed to smoothly proceed. As solvents, those with which the released by-produced glycol can be distilled off effectively at a low temperature by azeotropic distillation are preferred. Examples thereof include chlorobenzene, toluene, anisole, methylcyclohexane, isopentyl acetate, heptane, styrene, ethylbenzene, o-xylene, m-xylene, p-xylene, propylbenzene, tetrachloroethylene, and 1,1,2,2,-tetrachloroethane.

The ester interchange reaction can be carried out in an absence of a catalyst, but it is desirable to use an ester interchange catalyst. As the catalysts, acid catalysts such as organic acids, inorganic acids, Lewis acids, etc., are preferably used. Specifically, for example, p-toluenesulfonic acid, a cation-exchange resin, benzoic acid, acetic acid, sulfuric acid, phoshoric acid, zinc chloride, aluminum chloride, etc., are preferably used. The amount of the catalyst used is generally in an amount of from 0.001 to 5 mol%, and preferably from 0.1 to 2 mol%, based on the amount of the raw material spiro-orthocarbonate.

The reaction temperature can be varied according to the presence or absence of the solvent, the kind thereof, etc., but it is generally in a range of from 50° C. to 240° C., and more preferably from 90° C. to 180° C. If the reaction temperature is too low, the reaction rate is low, and if the reaction temperature is too high, the product or the raw material spiro-orthocarbonate decomposes. Accordingly such very high or very low temperatures are not preferred.

In the process of the present invention, a de-glycol reaction is utilized and the by-produced glycol is generally removed from the system. The progress of the reaction can be determined by measuring the amount of distilled glycol in the case that the by-produced glycol is distilled off by azeotropic distillation to separate the by-produced glycol from the solvent. In addition, it can be determined by analyzing the reaction solution by liquid chromatography or gas chromatography.

The spiro-orthocarbonate produced can be separated from the reaction solution by vacuum distillation, sublimation, or recrystallization, according to its properties after, if necessary, the reaction solution is subjected to neutralization processing with a basic substance such as amine, etc. in the case of using an acid catalyst in the reaction.

In the following, the process of the present invention is illustrated in greater detail by reference to examples. Substances used in the examples are descrbed by the following abbreviations:
1,4,6,9-Tetraoxaspiro[4.4]nonane: [4.4]N 2-Methyl-1,4,6,9-tetraoxaspiro[4.4]nonane: MM[4.4]N
2,7-Dimethyl-1,4,6,9-tetraoxaspiro[4.4]nonane: DM[4.4]N
2-Chloromethyl-1,4,6,9-tetroxaspiro[4.4]nonane: CM[4.4]N
1,3-Propanediol: PDO
1,3-Butanediol: BDO
2-Ethyl-1,3-hexanediol: EHDO
Neopentyl glycol: NPG
5-Norbornene-2,2-dimethanol: NDM
2,2-Dibromomethyl-1,3-propanediol: DBNPG
3-Cyclohexene-1,1-dimethanol: CDM
p-Toluenesulfonic acid monohydrate: p-TSA

EXAMPLE 1

3.96 g (0.030 mols) of [4.4]N, 8.33 g (0.054 mols) of NDM, 0.0285 g ($1.50 \times 10^{-4}$ mols) of p-TSA and 35 ml of xylene were placed in a three-neck flask equipped with a condenser, a stirrer and an inlet for blowing nitrogen, and the reaction was carried out at an oil bath temperature of 110° C. for 5 hours in a nitrogen stream. After the reaction was stopped by adding 0.06 ml of triethylamine, the contents were cooled with ice-water for 3 hours to sufficiently precipitate solid. The solid was separated from the reaction solution by filtration. This solid was then washed with methanol and recrystallized from chloroform, to obtain 4.53 g of colorless rod-shaped crystals.

This crystal was identified as 1,4:13,16-dimethano-8,10,19,20-tetraoxatrispiro[5.2.2.5.2.2]heneicosane-2,14-diene (hereinafter referred to as DN[5.5]U) by measuring the melting point, nuclear magnetic resonance (hereinafter referred to as NMR) spectrum and infrared absorption (hereinafter referred to as IR) spectrum. The yield thereof was 53% on the basis of the NDM used.

Detailed physical properties of DN[5.5]U are as follows:

Melting point 270°–275° C.
NMR spectrum: (in CDCl$_3$)

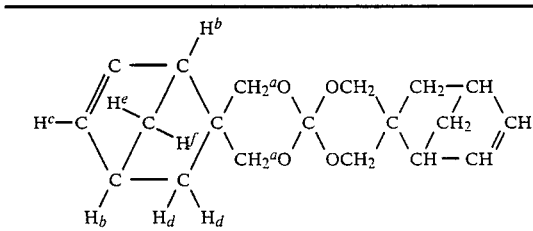

| δ (ppm) | Proton |
|---------|--------|
| 0.8–1.0 | f (2H) |
| 1.35–1.65 | d,e (6H) |
| 2.7–3.0 | b (4H) |
| 3.55–4.1 | a (8H) |
| 6.0–6.25 | c (4H) |

IR spectrum: (KBr method): 1215, 1020 cm$^{-1}$ (C—O—C); 1630 cm$^{-1}$ (C=C).

EXAMPLE 2

9.25 g (0.060 mols) of NDM, 4.82 g (0.033 mols) of NM[4.4]N, 0.0314 g ($1.65 \times 10^{-4}$ mols) of p-TSA and 40 ml of m-xylene were placed in a three-neck flask equipped with a water quantitative receiver equipped with a condenser, a stirrer and an inlet for blowing nitrogen, and the reaction was carried out at an oil bath temperature of 160° C. for 3.5 hours in a nitrogen stream. The amount of distilled glycol was 3.45 ml. m-Xylene was then removed from the reaction solution under reduced pressure, and the resulting residue was washed with a small amount of methanol to obtain 8.46 g of white crystals.

These crystals had a melting point of about 275° C. and were identified as DN[5.5]U. The yield thereof was 89% based on the NDN used.

EXAMPLE 3

9.25 g (0.060 mols) of NDM, 5.29 g (0.033 mols) of DM[4.4]N, 0.0314 g ($1.65 \times 10^{-4}$ mols) of p-TSA and 40 ml of toluene were placed in a three-neck flask equipped with a water quantitative receiver equipped with a condenser, a stirrer and an inlet for blowing nitrogen, and the reaction was carried out at an oil bath temperature of from 120° C. to 125° C. for 9 hours in a nitrogen stream. The amount of distilled glycol was 3.5 ml. Toluene was then removed from the reaction solution in a reduced pressure, and the resulting residue was washed with a small amount of methanol to obtain 6.48 g of white crystals.

These crystals had a melting point of about 265° C. and were identified as DN[5.5]U. The yield thereof was 68% based on the NDM used.

EXAMPLE 4

6.25 g (0.060 mols) of NPG, 4.82 g (0.033 mols) of MM[4.4]M, 0.0314 g ($1.65 \times 10^{-4}$ mols) of p-TSA and 40 ml of m-xylene were placed in a three-neck flask equipped with a water quantitative receiver equipped with a condenser, a stirrer and an inlet for blowing nitrogen, and the reaction was carried out at an oil bath temperature of 160° C. for 4 hours in a nitrogen stream. The amount of distilled glycol was 3.7 ml. m-Xylene was then removed from the reaction solution in a reduced pressure, and the resulting residue was purified by recrystallization with n-hexane to obtain 3.11 g of white crystals.

This crystal was identified as 3,3,9,9-tetramethyl-1,4,6,9-tetraoxaspiro[5.5]undecane (hereinafter referred to as TM[5.5]U) by measuring the melting point, NMR spectrum and IR spectrum. The yield thereof was 48% based on the NPG used.

Detailed physical properties of the TM[5.5]U are as follows.

Melting point: 144°–145° C.
NMR spectrum: (in CDCl$_3$)

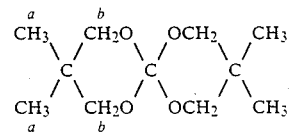

| δ (ppm) | Proton |
|---------|--------|
| 0.98 | a (12H) |
| 3.57 | b (8H) |

IR spectrum: (KBr method): 1075, 1205 cm$^{-1}$ (C—O—C).

EXAMPLE 5

13.16 g (0.090 mols) of EHDO, 7.23 g (0.0495 mols) of MM[4.4]N, 0.0471 g ($2.48 \times 10^{-4}$ mols) of p-TSA and 60 ml of m-xylene were placed in a three-neck flask equipped with a water quantitative receiver equipped with a condenser, a stirrerr and an inlet for blowing nitrogen, and the reaction was carried out at an oil bath temperature of 160° C. in a nitrogen stream for 5 hours. Distilled glycol was 4.7 ml. m-Xylene was then removed from the reaction solution in a reduced pressure. To the resulting residue, 40 ml of methylene chloride was added, and the resulting solution was washed 6 times with 15 ml portions of water. The washed reaction solution was dehydrated with anhydrous magnesium sulfate and thereafter the solvent was removed to obtain 12.2 g of a purified product.

This purified product was identified as 3,9-diethyl-2,8-dipropyl-1,5,7,11-tetraoxaspiro[5.5]undecane by NMR and IR spectra. The yield thereof was 90% based on the EHDO used.

Detailed physical properties of this compound are as follows.

NMR spectrum; (refer to FIG. 1) (in CDCl$_3$)

$$CH_3{}^a{-}CH_2{}^b{-}CH^b \diagup \begin{smallmatrix}CH_2{}^cO\\ \\CH^cO\end{smallmatrix} \diagdown C \diagup \begin{smallmatrix}OCH_2\\ \\OCH\end{smallmatrix} \diagdown CH{-}CH_2{-}CH_3$$

with side chains $CH_2{}^b$–$CH_{2b}$–$CH_{3a}$ and $CH_2$–$CH_2$–$CH_3$

| δ (ppm) | Proton |
|---------|--------|
| 0.7–1.1 | a (12H) |
| 1.1–1.8 | b (14H) |
| 3.3–4.3 | c (6H) |

Figure 2:
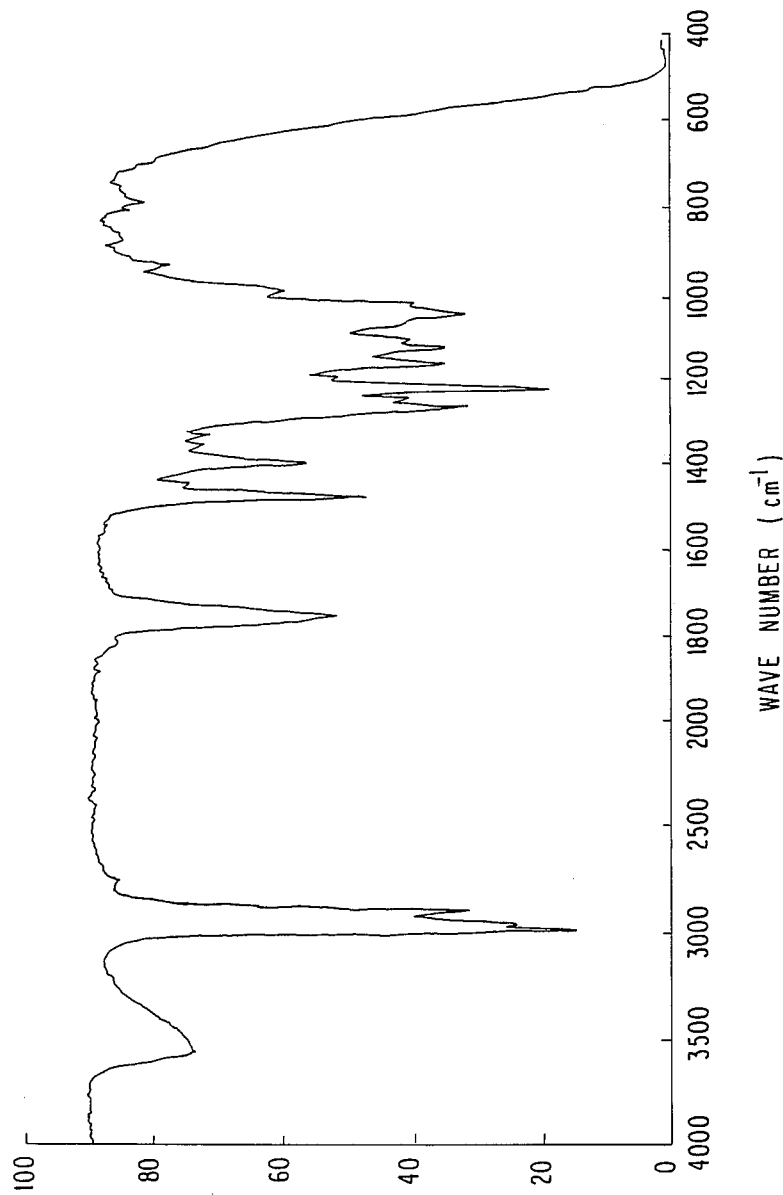
FIG. 2 is an IR spectrum of the same compound.

IR spectrum; (refer to FIG. 2) (Liquid membrane method): 1045, 1220 cm$^{-1}$ (C—O—C).

EXAMPLE 6

An ester interchange reaction was carried out in the same manner as in Example 5 except for using BDO as the raw material glycol. After the solvent was removed, the resulting residue was analyzed by gas chromatography. Thus, it was ascertained that 2,8-dimethyl-1,5,7,11-tetraoxaspiro[5.5]undecane (hereinafter referred to as DM[5.5]U) was obtained in a yield of about 54% based on the BDO used. Identification of this product was carried out by comparison of retention time by gas chromatographic analysis between it and DM[5.5]U identified previously which had been synthesized by another method.

EXAMPLE 7

An ester interchange reaction was carried out in the same manner as in Example 5 except for using PDO as the raw material glycol. After the solvent was removed, the resulting residue was analyzed by gas chromatography. Thus, it was ascertained that 1,5,7,11-tetraoxaspiro[5.5]undecane was obtained in a yield of about 43% based on the PDO used. Identification of this product was carried out by comparison of retention time by gas chromatographic analysis between it and 1,5,7,11-tetraoxaspiro[5.5]undecane identified previously which had been synthesized by another method.

EXAMPLE 8

Ester interchange was carried out by the process under the condition according to the above described examples, except that the kind of the raw material spiro-orthocarbonate, the raw material glycol and the reaction solvent, and the combinations thereof, were varied.

The results obtained are shown in the following table. In the table, values shown in parenthesis ( ) means yield. With respect to DM[5.5]U, the yield was determined by gas chromatography.

| Raw material spiro-ortho-carbonate/solvent | Raw material glycol | | |
|---|---|---|---|
| | NDM | NPG | BDO |
| DM[4.4]N/m-xylene | DN[5.5]U (69%) | TM[5.5]U (32%) | — |
| MM[4.4]N/p-xylene | — | — | DM[5.5]U (48%) |
| CM[4.4]N/xylene | DN[5.5]U (30%) | — | — |
| MM[4.4]N/toluene | DN[5.5]U (91%) | TM[5.5]U (56%) | DM[5.5]U (35%) |

EXAMPLE 9

15.72 g (0.060 mols) of DBNPG, 4.90 g of a mixture of [4.4]N, MM[4.4]N and DM[4.4]N (weight ratio 1/2/1), 0.0314 g (1.65×10$^{-4}$ mols) of p-TA as a catalyst and 40 ml of m-xylene as a solvent were placed in a three-neck flask equipped with a water quantitative receiver equipped with a condenser, a stirrer and an inlet for blowing nitrogen, and the de-glycol reaction was carried out under reflux condition at an oil bath temperature of 180° C. for 6 hours in a nitrogen stream. m-Xylene was then removed from the reaction solution under reduced pressure, and the resulting residue (light-yellow solid) was purified by recrystallization from acetone and from a mixture of acetone and n-hexane in sequence, to obtain colorless flaky crystals.

This crystal was identified as 3,3,9,9-tetrabromomethyl-1,5,7,11-tetraoxaspiro[5.5]undecane by measuring the melting point, NMR spectrum and IR spectrum. The yield thereof was 40.7% based on the DBNPG used.

Detailed physical properties of the reaction product are as follows.

Melting point: 126.5°–128.5° C.

NMR spectrum: (in CDCl$_3$)

$$BrCH_2{}^a \diagup \begin{smallmatrix}CH_2O\\ \\CH_2O\end{smallmatrix}{}^b \diagdown C \diagup \begin{smallmatrix}OCH_2\\ \\OCH_2\end{smallmatrix}{}^b \diagdown CH_2Br{}^a$$

| δ (ppm) | Proton |
|---------|--------|
| 3.50 | a (8H) |
| 3.88 | b (8H) |

IR spectrum (KBr method): 1035, 1205 cm$^{-1}$ (C—O—C).

EXAMPLE 10

An ester interchange reaction was carried out in the same manner as in Example 9 except for using CDM as the raw material glycol and an industrially used mixed xylene as the solvent in place of DBNPG and m-xylene, respectively. After the reaction was completed, 75% of the mixed xylene used was removed from the reaction solution, followed by cooling. The resulting crystals thus precipitated were collected by filtration and dried to obtain a crude reaction product having a melting point of 107° C. to 115° C. The reaction product was then purified by recrystallization from acetone to obtain colorless plate-shaped crystals.

This crystal was identified as 8,10,19,20-tetraoxatrispiro[5.2.2.5.2.2]heneicosane-2,14-diene by measuring the melting point, NMR spectrum and IR spectrum. The yield thereof was 79% based on the CDM used.

Detailed physical properties of the reaction product are as follows.

Melting point: 120°–121° C.
NMR spectrum: (in $CDCl_3$)

$$\begin{array}{c} \overset{c}{CH} - \overset{b}{CH_2} \quad \overset{a}{CH_2O} \quad OCH_2 \quad CH_2-CH_2 \\ c \parallel \diagdown \diagup \diagdown \diagup \diagdown \diagup \diagdown \\ CH \quad\quad C \quad\quad C \quad\quad C \quad\quad CH \\ \diagdown \;_b\; \diagup \;_d\; \diagdown \;_a\; \diagup \diagdown \diagup \diagdown \;_c\; \parallel \\ CH_2-CH_2 \quad CH_2O \quad OCH_2 \quad CH_2-CH \end{array}$$

| δ (ppm) | Proton |
|---------|--------|
| 1.50–1.72 | d (4H) |
| 1.80–2.20 | b (8H) |
| 3.73 | a (8H) |
| 5.63 | c (4H) |

IR spectrum: (KBr method): 1035, 1210 $cm^{-1}$ (C—O—C).

As is described above, according to the process of the present invention, various spiro-orthocarbonates can be easily and cheaply produced in high yield when a spiro-orthocarbonate, e.g., one produced from epoxide and cyclic carbonate, is subjected to an ester interchange reaction with diol.

The present invention is an effective placement for the prior process for producing spiro-orthocarbonate, which was not practical as an industrial process, and thus production of industrially useful spiro-orthocarbonate, which are known as substance showing expansion of volume upon polymerization, can be usefully carried out according to the present invention.

While the invention has been described in detail and with reference to specific embodiments thereof, it will be apparent to one skilled in the art that various changes and modifications can be made therein without departing from the spirit and scope thereof.

What is claimed is:

1. A process for producing a spiro-orthocarbonate having glycol unit (2), which comrises reacting a spiro-orthocarbonate having glycol unit (1) which is different from glycol unit (2), with a glycol having glycol unit (2) to release a glycol having glycol unit (1).

2. A process according to claim 1, wherein the glycol having glycol unit (2) has a higher boiling point than that of the released glycol having glycol unit (1).

3. A process according to claim 2, wherein the reaction is carried out while removing the released glycol having glycol unit (1).

4. A process according to claim 1, wherein the spiro-orthocarbonate having glycol unit (1) is 1,4,6,9-tetraoxaspiro[4.4]nonane or a derivative thereof.

5. A process according to claim 2, wherein the spiro-orthocarbonate having glycol unit (1) is 1,4,6,9-tetraoxaspiro[4.4]nonane or a derivative thereof.

6. A process according to claim 3, wherein the spiro-orthocarbonate having glycol unit (1) is 1,4,6,9-tetraoxaspiro[4.4]nonane or a derivative thereof.

7. A process according to claim 4, wherein the glycol having glycol unit (2) is 1,3-diol.

8. A process according to claim 5, wherein the glycol having glycol unit (2) is a 1,3-diol.

9. A process according to claim 6, wherein the glycol having glycol unit (2) is a 1,3-diol.

10. A process according to claim 7, wherein an ester interchange catalyst is used.

11. A process according to claim 8, wherein an ester interchange catalyst is used.

12. A process according to claim 9, wherein an ester interchange catalyst is used.

13. A process according to claim 3, wherein the glycol having glycol unit (1) is removed by distillation with a solvent.

14. A process according to claim 13, wherein the solvent is selected from the group consisting of chlorobenzene, toluene, anisole, methylcyclohexane, isopentyl acetate, heptane, styrene, ethylbenzene, o-xylene, m-xylene, p-xylene, propylbenzene, tetrachloroethylene, and 1,1,2,2-tetrachloroethane.

15. A process according to claim 1, wherein the glycol having glycol unit (2) used in an amount of 6 mols or less per mol of the spiro-orthocarbonate having glycol unit (1).

16. A process according to claim 1, wherein the glycol having glycol unit (2) is used in an amount of from 0.7 to 2.4 mols per mol of the spiro-orthocarbonate having glycol unit (1).

17. A process according to claim 10, wherein the catalyst is selected from the group consisting of p-toluenesulfonic acid, a cation-exchange resin, benzoic acid, acetic acid, sulfuric acid, phosphoric acid, zinc chloride, and aluminum chloride.

18. A process as in claim 10, wherein the catalyst is used in an amount of from 0.001 to 5 mol%, based on the amount of the spiro-orthocarbonate having glycol unit (1).

19. A process as in claim 10, wherein the catalyst is used in an amount of from 0.1 to 2 mol%, based on the amount of the spiro-orthocarbonate having glycol unit (1).

* * * * *